(12) United States Patent
Liu et al.

(10) Patent No.: US 10,173,965 B2
(45) Date of Patent: Jan. 8, 2019

(54) METHOD FOR PREPARING PREGABALIN INTERMEDIATE 3-CARBAMOYMETHYL-5-METHYLHEXANOIC ACID WITHOUT SOLVENT

(71) Applicant: ZHEJIANG HUAHAI PHARMACEUTICAL CO., LTD, Linhai (CN)

(72) Inventors: Musong Liu, Linhai (CN); Wenling Zhang, Linhai (CN); Peng Wang, Linhai (CN)

(73) Assignee: ZHEJIANG HUAHAI PHARMACEUTICAL CO., LTD., Zhejiang (CN)

( * ) Notice: Subject to any disclaimer, the term of this patent is extended or adjusted under 35 U.S.C. 154(b) by 0 days.

(21) Appl. No.: 15/544,095

(22) PCT Filed: Mar. 25, 2016

(86) PCT No.: PCT/CN2016/077338
§ 371 (c)(1),
(2) Date: Jul. 17, 2017

(87) PCT Pub. No.: WO2016/155566
PCT Pub. Date: Oct. 6, 2016

(65) Prior Publication Data
US 2017/0369422 A1 Dec. 28, 2017

(30) Foreign Application Priority Data
Mar. 27, 2015 (CN) .......................... 2015 1 0138771

(51) Int. Cl.
*C07C 231/02* (2006.01)
*C07C 231/24* (2006.01)
*C07C 233/05* (2006.01)

(52) U.S. Cl.
CPC .......... *C07C 231/02* (2013.01); *C07C 231/24* (2013.01)

(58) Field of Classification Search
CPC .... C07C 231/02; C07C 233/05; C07C 231/24
See application file for complete search history.

(56) References Cited

U.S. PATENT DOCUMENTS 5,629,447 A * 5/1997 Huckabee ............. C07C 211/27
562/553

FOREIGN PATENT DOCUMENTS

| CN | 101448779 A | 6/2009 |
| CN | 101987826 A | 3/2011 |
| WO | 2012093411 A2 | 7/2012 |

* cited by examiner

*Primary Examiner* — Pancham Bakshi
*Assistant Examiner* — Mark R Luderer
(74) *Attorney, Agent, or Firm* — McCarter & English, LLP; Steven G. Davis; Wei Song

(57) ABSTRACT

The present invention provides a method for preparing a pregabalin intermediate 3-carbamoymethyl-5-methylhexanoic acid without solvent. The method comprises the following steps: a) cooling an ammonia water system to a certain temperature; b) adding 3-isobutylglutaric anhydride dropwise to the system, then keeping temperature, and reacting; c) after completing the reaction, adding an acid to the system to adjust pH; d) after adjusting pH, cooling, then keeping temperature, crystallizing, then suction filtering and drying; and e) adding a solvent to the dried substance, slurrying, and suction filtering and drying to obtain the final product. The method provided in the present invention for preparing 3-carbamoymethyl-5-methylhexanoic acid is high-yield, green, environmentally-friendly, simple and convenient, and of less pollution.

20 Claims, No Drawings

METHOD FOR PREPARING PREGABALIN INTERMEDIATE 3-CARBAMOYMETHYL-5-METHYLHEXANOIC ACID WITHOUT SOLVENT

CROSS-REFERENCE TO RELATED APPLICATIONS

The present application is a U.S. national stage application filed under 35 U.S.C. § 371(c), of International Application No. PCT/CN2016/077338, filed on Mar. 25, 2016, which claims the priority of Chinese Patent Application No. 201510138771.1, titled "Method for preparing 3-carbamoymethyl-5-methylhexanoic acid without solvent", filed on Mar. 27, 2015 before the State Intellectual Property Office of China. The entire contents of each of the aforementioned applications are incorporated herein by reference.

TECHNICAL FIELD

The present invention relates to the field of preparing pharmaceutical and chemical intermediates, and particularly to a method for preparing 3-carbamoymethyl-5-methylhexanoic acid without solvent.

BACKGROUND

Epilepsy is one of the oldest diseases in the world. According to reports of the World Health Organization, the number of patients worldwide is up to 50 million, and there are 6000 new cases every day. The epidemiological data of China shows that, in China, the total prevalence rate of epilepsy is 7 ‰, the annual incidence rate is 28.8 per 100 thousand, the prevalence rate of "active epilepsy" is 4.6 ‰, and the prevalence rate of active epilepsy, the seizure of which has been occurred within 2 and 5 years, is 4.9 ‰ and 5.4 ‰, respectively. Accordingly, it is estimated that there are about 9 million epilepsy patients in China, wherein about 4 million patients fail to receive normal treatment, and there are about 400 thousands new epilepsy patients in China every year. Therefore, the health administrators, medical and scientific researchers, and social workers in China are facing great challenges in the field of epilepsy.

Pregabalin, an agonist of the GABA receptor developed by Pfizer, was approved in June 2005 for adjuvant therapy for local seizure epilepsy of adults, which is the most promising one of the developed drugs for treating epilepsy. Compared with gabapentin, pregabalin has stronger anti-convulsive effect, fewer side effects, less dosage, fewer taking times, and also has anti-anxiety effect and other advantages. Moreover, it has no interaction with the existing antiepileptic drugs, thus it is easy to combine with other antiepileptic drugs for synergistic treatment of epilepsy. Meanwhile, this product is also a therapeutic drug for diabetic peripheral neuropathy-related neuralgia, herpes zoster neuralgia, fibromyalgia and alike. It is used in a wide range of people, and has broad market prospect. This drug is considered as a blockbuster drug once marketed. Some analysts predicted that the market would reach 10 billion US dollars by 2016.

Currently, there are two main types of methods reported for preparing pregabalin intermediate 3-carbamoymethyl-5-methylhexanoic acid. One is to obtain 3-carbamoymethyl-5-methylhexanoic acid by ammonolysis of 3-isobutylglutaric anhydride (Compound 1) in the presence of certain organic solvents and under the condition of ammonia water. The other is to obtain 3-carbamoymethyl-5-methylhexanoic acid by racemic recovery of the mother liquor after resolution.

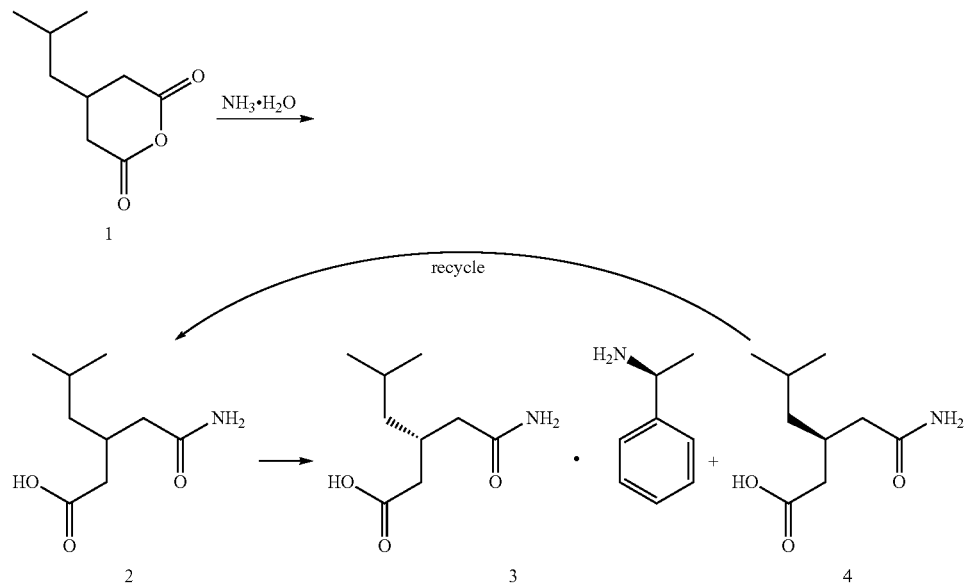

However, the methods of the first type reported currently in literatures are adding certain organic solvents as reaction medium, wherein the most common solvent is methyl tert-butyl ether (see for example, PCT International Application WO2012093411 A2 filed by Dr. Braja Sundar Pradhan in 2012). It is also reported in several domestic literatures, but methyl tert-butyl ether is added into each of the systems for preparing 3-carbamoymethyl-5-methylhexanoic acid as a solvent.

SUMMARY OF THE INVENTION

An object of the present invention is to provide a method for preparing a pregabalin intermediate 3-carbamoymethyl-5-methylhexanoic acid without solvent, which comprises the following steps:
1) cooling an ammonia water system to a certain temperature;
2) adding 3-isobutylglutaric anhydride dropwise to the system, then keeping temperature, and reacting;
3) after completing the reaction, adding an acid to the system to adjust pH;
4) after adjusting pH, cooling, then keeping temperature, crystallizing, then suction filtering and drying; and
5) adding a solvent to the dried substance, slurrying, and suction filtering and drying to obtain the final product.

In one embodiment, the certain temperature of the above step 1) is 0 to 20° C., and the amount of the ammonia water used by weight is 0.9 to 1.1 times of the weight of 3-isobutylglutaric anhydride.

In another embodiment, the duration for keeping temperature and reacting in step 2) is 2 to 4 h.

In yet another embodiment, in the above step 3), the pH is adjusted in the range of 2 to 4.

In another embodiment, in the above step 4), it is cooled to 0 to 10° C.

In yet another embodiment, in the above step 5), the solvent for slurrying is ethyl acetate, dichloromethane, toluene, or any combination thereof. In another embodiment, the volume dosage of the solvent for slurrying is 2 to 5 times of the weight of the dried substance in ml/g. In yet another embodiment, slurrying is performed at a temperature of 25 to 35° C. In another embodiment, the duration for slurrying is 0.5 to 2 h.

According to the present invention, the expression "without solvent" means that no organic solvent such as methyl tert-butyl ether is used in the reaction process for preparing 3-carbamoymethyl-5-methylhexanoic acid.

According to the method of the present invention, 3-isobutylglutaric anhydride reacts directly with ammonia water without adding a solvent. After completing the reaction, 3-carbamoymethyl-5-methylhexanoic acid is obtained by simple treatments. Compared with the prior art, the present invention has the following obvious advantages: (1) compared with the conventional methods for preparing 3-carbamoymethyl-5-methylhexanoic acid which use organic solvent in the reaction process, the method of the present invention without organic solvent in the reaction process, can obtain a much higher yield of 3-carbamoymethyl-5-methylhexanoic acid; (2) the method according to the present invention does not require using organic solvent in the reaction process, and it is green and pollution-free, thus environmentally-friendly; (3) the method according to the present invention does not require using special equipment and devices, thus it is simple and convenient; (4) the method according to the present invention without organic solvent in the reaction process is cost-saving, which has big advantages on the cost of industrialized products. In summary, the method provided in the present invention for preparing 3-carbamoymethyl-5-methylhexanoic acid is high-yield, green, environmentally-friendly, simple and convenient, and of less pollution.

DETAILED DESCRIPTION OF THE INVENTION

To make the objects, technical solutions and advantages of the present invention more clearly, the present invention will be described in further detail with reference to the following examples. Obviously, the described examples are only part of the examples of the present invention, rather than all examples. Based on examples in the present invention, all other examples obtained by those skilled in the art without creative work are within the protection scope of the present invention.

The present invention is further illustrated by the following examples, but these examples are not intended to limit the present invention in any way.

EXAMPLE 1

100 g of ammonia water was added to a 500 ml four-necked flask. After completing the addition, the four-necked flask was cooled to 5° C. When cooling to 5° C., 100 g of 3-isobutylglutaric anhydride was added to the four-necked flask dropwise. The temperature of the system was controlled at 0~20° C. during the addition of anhydride. After completing the dropwise addition, it was kept temperature and reacted for 4 h. Then hydrochloric acid was added dropwise to adjust pH to 3.5. After adjusting pH, it was cooled to 10° C., kept temperature and stirred for 1 h, and then suction filtered to obtain a filter cake. The filter cake was dried to obtain 107.3 g substance, transferred to a 500 ml single-necked flask, and 250 ml of methylene chloride was added. It was heated to 30° C., slurried for 1 h, suction filtered and dried to obtain 104.5 g product. The yield was 95% and the purity was 99.7%.

EXAMPLE 2

100 g of ammonia water was added to a 500 ml four-necked flask. After completing the addition, the four-necked flask was cooled to 10° C. When cooling to 5° C., 100 g of 3-isobutylglutaric anhydride was added to the four-necked flask dropwise. The temperature of the system was controlled at 0-20° C. during the addition of anhydride. After completing the dropwise addition, it was kept temperature and reacted for 3 h. Then hydrochloric acid was added dropwise to adjust pH to 2. After adjusting pH, it was cooled to 5° C., kept temperature and stirred for 1 h, and then suction filtered to obtain a filter cake. The filter cake was dried to 107.8 g substance, transferred to a 500 ml single-necked flask, and 300 ml of methylene chloride was added. It was heated to 25° C., pulped for 1.5 h, suction filtered and dried to obtain 104.8 g product. The yield was 95.3% and the purity was 99.8%.

EXAMPLE 3

100 g of ammonia water was added to a 500 ml four-necked flask. After completing the addition, the four-necked flask was cooled to 5° C. When cooling to 5° C., 100 g of 3-isobutylglutaric anhydride was added to the four-necked flask dropwise. The temperature of the system was controlled at 0~20° C. during the addition of anhydride. After completing the dropwise addition, it was kept temperature and reacted for 4 h. Then hydrochloric acid was added dropwise to adjust pH to 3.5. After adjusting pH, it was cooled to 10° C., kept temperature and stirred for 1 h, and then suction filtered to obtain a filter cake. The filter cake was dried to 107.5 g substance, transferred to a 500 ml single-necked flask, and 380 ml of methylene chloride was added. It was heated to 28° C., pulped for 0.5 h, suction filtered and dried to obtain 103.2 g product. The yield was 93.8% and the purity was 99.7%.

EXAMPLE 4

100 g of ammonia water was added to a 500 ml four-necked flask. After completing the addition, the four-necked flask was cooled to 5° C. When cooling to 5° C., 100 g of 3-isobutylglutaric anhydride was added to the four-necked flask dropwise. The temperature of the system was controlled at 0~20° C. during the addition of anhydride. After completing the dropwise addition, it was kept temperature and reacted for 2.5 h. Then hydrochloric acid was added dropwise to adjust pH to 2. After adjusting pH, it was cooled to 10° C., kept temperature and stirred for 1 h, and then suction filtered to obtain a filter cake. The filter cake was dried to 107.9 g substance, transferred to a 500 ml single-necked flask, and 280 ml of methylene chloride was added. It was heated to 30° C., pulped for 1 h, suction filtered and dried to obtain 107.5 g product. The yield was 97.7% and the purity was 99.9%.

EXAMPLE 5

100 g of ammonia water was added to a 500 ml four-necked flask. After completing the addition, the four-necked flask was cooled to 5° C. When cooling to 5° C., 100 g of 3-isobutylglutaric anhydride was added to the four-necked flask dropwise. The temperature of the system was controlled at 0~20° C. during the addition of anhydride. After completing the dropwise addition, it was kept temperature and reacted for 2 h. Then hydrochloric acid was added dropwise to adjust pH to 3.0. After adjusting pH, it was cooled to 0° C., kept temperature and stirred for 1 h, and then suction filtered to obtain a filter cake. The filter cake was dried to 108.5 g substance, transferred to a 500 ml single-necked flask, and 250 ml of ethyl acetate was added. It was heated to 30° C., pulped for 1 h, suction filtered and dried to obtain 106.5 g product. The yield was 96.8% and the purity was 99.8%.

EXAMPLE 6

100 g of ammonia water was added to a 500 ml four-necked flask. After completing the addition, the four-necked flask was cooled to 5° C. When cooling to 5° C., 100 g of 3-isobutylglutaric anhydride was added to the four-necked flask dropwise. The temperature of the system was controlled at 0~20° C. during the addition of anhydride. After completing the dropwise addition, it was kept temperature and reacted for 3 h. Then hydrochloric acid was added dropwise to adjust pH to 3.5. After adjusting pH, it was cooled to 5° C., kept temperature and stirred for 1 h, and then suction filtered to obtain a filter cake. The filter cake was dried to 107.0 g substance, transferred to a 500 ml single-necked flask, and 330 ml of ethyl acetate was added. It was heated to 30° C., pulped for 1 h, suction filtered and dried to obtain 104.0 g product. The yield was 94.5% and the purity was 99.9%.

EXAMPLE 7

100 g of ammonia water was added to a 500 ml four-necked flask. After completing the addition, the four-necked flask was cooled to 5° C. When cooling to 5° C., 100 g of 3-isobutylglutaric anhydride was added to the four-necked flask dropwise. The temperature of the system was controlled at 0~20° C. during the addition of anhydride. After completing the dropwise addition, it was kept temperature and reacted for 4 h. Then hydrochloric acid was added dropwise to adjust pH to 2.5. After adjusting pH, it was cooled to 3° C., kept temperature and stirred for 1 h, and then suction filtered to obtain a filter cake. The filter cake was dried to 107.5 g substance, transferred to a 500 ml single-necked flask, and 350 ml of ethyl acetate was added. It was heated to 30° C., pulped for 0.5 h, suction filtered and dried to obtain 104.8 g product. The yield was 95.3% and the purity was 99.8%.

EXAMPLE 8

100 g of ammonia water was added to a 500 ml four-necked flask. After completing the addition, the four-necked flask was cooled to 5° C. When cooling to 5° C., 100 g of 3-isobutylglutaric anhydride was added to the four-necked flask dropwise. The temperature of the system was controlled at 0~20° C. during the addition of anhydride. After completing the dropwise addition, it was kept temperature and reacted for 4 h. Then hydrochloric acid was added dropwise to adjust pH to 4.0. After adjusting pH, it was cooled to 2° C., kept temperature and stirred for 1.5 h, and then suction filtered to obtain a filter cake. The filter cake was dried to 107.3 g substance, transferred to a 500 ml single-necked flask, and 280 ml of ethyl acetate was added. It was heated to 25° C., pulped for 1.5 h, suction filtered and dried to obtain 105.1 g product. The yield was 95.6% and the purity was 99.7%.

EXAMPLE 9

100 g of ammonia water was added to a 500 ml four-necked flask. After completing the addition, the four-necked flask was cooled to 5° C. When cooling to 5° C., 100 g of 3-isobutylglutaric anhydride was added to the four-necked flask dropwise. The temperature of the system was controlled at 0~20° C. during the addition of anhydride. After completing the dropwise addition, it was kept temperature and reacted for 2.5 h. Then hydrochloric acid was added dropwise to adjust pH to 2.0. After adjusting pH, it was cooled to 10° C., kept temperature and stirred for 1 h, and then suction filtered to obtain a filter cake. The filter cake was dried to 108.5 g substance, transferred to a 500 ml single-necked flask, and 320 ml of toluene was added. It was heated to 30° C. pulped for 0.5 h, suction filtered and dried to obtain 106.25 g product. The yield was 96.5% and purity was 99.7%.

EXAMPLE 10

100 g of ammonia water was added to a 500 ml four-necked flask. After completing the addition, the temperature of the four-necked flask was cooled to 5° C. When cooling to 5° C., 100 g of 3-isobutylglutaric anhydride was added to the four-necked flask dropwise. The temperature of the system was controlled at 0~20° C. during the addition of anhydride. After completing the dropwise addition, it was kept temperature and reacted for 2.5 h. Then hydrochloric acid was added dropwise to adjust pH to 2.0. After adjusting pH, it was heated to 3° C., kept temperature and stirred for 1.5 h, and then suction filtered to obtain a filter cake. The filter cake was dried to 108.3 g substance, transferred to a 500 ml single-necked flask, and 250 ml of toluene was added. It was heated to 30° C., pulped for 1 h, suction filtered and dried to obtain 104.7 g product. The yield was 95.2% and the purity was 99.8%.

EXAMPLE 11

100 g of ammonia water was added to a 500 ml four-necked flask. After completing the addition, the four-necked flask was cooled to 8° C. When cooling to 5° C., 100 g of 3-isobutylglutaric anhydride was added to the four-necked flask dropwise. The temperature of the system was controlled at 0~20° C. during the addition of anhydride. After completing the dropwise addition, it was kept temperature and reacted for 4 h. Then hydrochloric acid was added dropwise to adjust pH to 3.5. After adjusting pH, it was cooled to 10° C., kept temperature and stirred for 1 h, and then suction filtered to obtain a filter cake. The filter cake was dried to 108.9 g substance, transferred to a 500 ml single-necked flask, and 380 ml of toluene was added. It was heated to 30° C., pulped for 1 h, suction filtered and dried to obtain 105.4 g product. The yield was 95.8% and the purity was 99.8%.

EXAMPLE 12

100 g of ammonia water was added to a 500 ml four-necked flask. After completing the addition, the four-necked flask was cooled to 3° C. When cooling to 5° C., 100 g of 3-isobutylglutaric anhydride was added to the four-necked flask dropwise. The temperature of the system was controlled at 0~20° C. during the addition of anhydride. After completing the dropwise addition, it was kept temperature and reacted for 3 h. Then hydrochloric acid was added dropwise to adjust pH to 2.5. After adjusting pH, it was cooled to 10° C., kept temperature and stirred for 1 h, and then suction filtered to obtain a filter cake. The filter cake was dried to 107.3 g substance, transferred to a 500 ml single-necked flask, and 340 ml of toluene was added. It was heated to 30° C., pulped for 1 h, suction filtered and dried to obtain 105.9 g product. The yield was 96.3% and the purity was 99.9/%.

COMPARATIVE EXAMPLE 1

The 3-carbamoymethyl-5-methylhexanoic acid was prepared in the same manner as described in Example 5 of WO2012093411A2. The yield was only 80.4%. It follows that the yield of the method for preparing 3-carbamoymethyl-5-methylhexanoic acid without solvent according to the present invention is much higher than that of the method described in the prior art.

The above examples are only the preferable examples of the invention, not intending to limit the present invention. Any modifications, equivalent substitutions, improvements and the like made within the spirit and principles of the invention, should be included in the protection scope of the present invention.

What is claimed is:

1. A method for preparing a pregabalin intermediate 3-carbamoymethyl-5-methylhexanoic acid, wherein the method comprises the following steps:
   1) cooling an ammonia water system to a certain temperature without an organic solvent;
   2) adding 3-isobutylglutaric anhydride dropwise to the system, then keeping a first temperature, and reacting without an organic solvent;
   3) after completing the reaction, adding an acid to the system to adjust pH;
   4) after adjusting pH, cooling, then keeping a second temperature, crystallizing, then suction filtering and drying to obtain a dried substance; and
   5) adding a solvent to the dried substance, slurrying, suction filtering and drying to obtain 3-carbamoymethyl-5-methylhexanoic acid.

2. The method according to claim 1, wherein the certain temperature of step 1) is 0 to 20° C., and the amount of the ammonia water used by weight is 0.9 to 1.1 times of the weight of 3-isobutylglutaric anhydride.

3. The method according to claim 1, wherein the duration for keeping the first temperature and reacting is 2 to 4 h in step 2).

4. The method according to claim 1, wherein the pH is adjusted in the range of 2 to 4 in step 3).

5. The method according to claim 1, wherein it is cooled to 0 to 10° C. in step 4).

6. The method according to claim 1, wherein the solvent for slurrying in step 5) is ethyl acetate, dichloromethane, toluene, or any combination thereof.

7. The method according to claim 1, wherein in step 5), the volume dosage of the solvent for slurrying is 2 to 5 times of the weight of the dried substance in ml/g; slurrying is performed at a temperature of 25 to 35° C.; and the duration for slurrying is 0.5 to 2 h.

8. The method according to claim 2, wherein the duration for keeping the first temperature and reacting is 2 to 4 h in step 2).

9. The method according to claim 2, wherein the pH is adjusted in the range of 2 to 4 in step 3).

10. The method according to claim 2, wherein it is cooled to 0 to 10° C. in step 4).

11. The method according to claim 2, wherein the solvent for slurrying in step 5) is ethyl acetate, dichloromethane, toluene, or any combination thereof.

12. The method according to claim 2, wherein in step 5), the volume dosage of the solvent for slurrying is 2 to 5 times of the weight of the dried substance in ml/g; slurrying is performed at a temperature of 25 to 35° C.; and the duration for slurrying is 0.5 to 2 h.

13. The method according to claim 3, wherein the pH is adjusted in the range of 2 to 4 in step 3).

14. The method according to claim 3, wherein it is cooled to 0 to 10° C. in step 4).

15. The method according to claim 3, wherein the solvent for slurrying in step 5) is ethyl acetate, dichloromethane, toluene, or any combination thereof.

16. The method according to claim 3, wherein in step 5), the volume dosage of the solvent for slurrying is 2 to 5 times of the weight of the dried substance in ml/g; slurrying is performed at a temperature of 25 to 35° C.; and the duration for slurrying is 0.5 to 2 h.

17. The method according to claim 4, wherein it is cooled to 0 to 10° C. in step 4).

18. The method according to claim 4, wherein the solvent for slurrying in step 5) is ethyl acetate, dichloromethane, toluene, or any combination thereof.

19. The method according to claim 4, wherein in step 5), the volume dosage of the solvent for slurrying is 2 to 5 times of the weight of the dried substance in ml/g; slurrying is performed at a temperature of 25 to 35° C.; and the duration for slurrying is 0.5 to 2 h.

20. The method according to claim 5, wherein the solvent for slurrying in step 5) is ethyl acetate, dichloromethane, toluene, or any combination thereof.

* * * * *